United States Patent [19]
Lee

[11] Patent Number: 6,162,460
[45] Date of Patent: Dec. 19, 2000

[54] POULTICE

[76] Inventor: Yang-Hee Lee, Kangnampark 101, 175-2, Poi-Dong, Kangnam-Ku, Seoul, Rep. of Korea

[21] Appl. No.: 09/041,053

[22] Filed: Mar. 10, 1998

[51] Int. Cl.[7] .................................................... A61N 2/04
[52] U.S. Cl. ................................. 424/449; 607/2; 607/3; 607/96; 607/100; 607/112
[58] Field of Search .................................. 602/2, 48, 52, 602/53, 54, 57, 58; 607/2, 3, 96, 100, 108, 112, 149, 152; 424/443, 447, 448, 449

[56] References Cited

U.S. PATENT DOCUMENTS

| | | | |
|---|---|---|---|
| 4,676,246 | 6/1987 | Korenaga | 128/399 |
| 5,133,351 | 7/1992 | Masaki | 607/3 |
| 5,800,481 | 9/1998 | Loos | 607/100 |

FOREIGN PATENT DOCUMENTS

| | | |
|---|---|---|
| 0 269 246 | 6/1988 | European Pat. Off. . |
| 0 547 482 | 6/1993 | European Pat. Off. . |
| WO 91/18642 | 12/1991 | WIPO . |
| WO 97/27899 | 8/1997 | WIPO . |

*Primary Examiner*—Robert H. Harrison
*Attorney, Agent, or Firm*—Birch, Stewart, Kolasch & Birch, LLP.

[57] ABSTRACT

Disclosed is a poultice capable of rapidly curing an affected part of a patient's body and of enhancing a curative value by increasing an infiltration efficiency of medicine into a hypodermic tissue of the affected part with the aid of a low-frequency electro therapy. Both surfaces of compress sheets of the poultice are coated with predetermined skin-adhesive medicines adapted to cure an affected part of a patient's body. A thin film is attached to lower surfaces of the compress sheets. The thin film can be detached from the lower surfaces of the compress sheets during use of the poultice. An attaching sheet for attaching the poultice to the affected part of the patient's body is located on upper surfaces of the compress sheets. A pair of conductive layers are coated on a lower surface of the attaching sheet, which is opposite to the upper surfaces of the compress sheets. A low-frequency oscillator for applying a low-frequency energy into the compress sheets is installed between the conductive layers. A push button for applying an operating signal to the low-frequency oscillator is installed on an upper surface of the low-frequency oscillator. Alternatively, a body-temperature sensing sensor or a shock sensing sensor for applying an operating signal to the low-frequency oscillator is installed on a lower surface of the low-frequency oscillator.

18 Claims, 6 Drawing Sheets

POULTICE

BACKGROUND OF THE INVENTION

1. Field of the Invention

The present invention relates to a poultice, and more particularly to a poultice capable of rapidly curing an affected part of a patient's body and of enhancing a curative value by increasing an infiltration efficiency of medicine into a hypodermic tissue of the affected part with the aid of a low-frequency electrotherapy

2. Description of Related Art

Generally, a poultice is used for curing pains such as a bruise, a muscular pain, an articular disease or neuralgia by simply attaching it on an affected part of a patient's body. The poultice has a compress sheet made of flexible woven stuff. One surface of the compress sheet is coated with skin-adhesive medicine and is covered with a flexible thin film of vinyl. The thin film can be detached from the compress sheet at the time that the patient attaches the poultice on the affected part of the patient's body.

When the patient wants to use the poultice as described above, the patient separates the thin film from the compress sheet first. Under this state, the patient attaches the one surface of the compress sheet, which is coated with skin-adhesive medicine, on the affected part of the patient's body. Then, the patient maintains the state that the compress sheet is attached to the affected part, during a predetermined time period. As a result, it is possible to cure the affected part of the patient's body due to infiltration and curative action of the medicine.

Since the poultice as described above cures the affected part of the patient's body only by the medical action of the medicine which is coated on the one surface of the compress sheet, the curative value is low and the infiltration property of the medicine gradually deteriorates as time goes by. Therefore, it is necessary that the patient replace the worn poultice with a new poultice after a lapse of certain hours. If much time has passed after the patient attached the poultice to the affected part, the poultice closes skin pores of the patient's body at its attaching position when the effect of the medicine disappears. As a result, the patient feels itchy. Further, if the patient uses the poultice as described above in order to cure the affected part of the patient's body, it is impossible to ascertain the time within which almost all of the medicine in the poultice is absorbed.

Meanwhile, in hospitals and the like, there are often used a variety of physical therapies for enhancing the curative value to the affected part of the patient's body. Among the physical therapies, a method of medical treatment not employing any poultice, but employing an apparatus for generating low-frequency energy, has been proposed. According to this method, the apparatus is brought into contact with the affected part of the patient's body under the state that a predetermined medicine is applied to the affected part of the patient's body. However, in this case, the cost of treatment is increased due to use of the expensive apparatus and thereby the patient must bear a heavy burden. Further, if the patient uses the method as described above in order to cure the affected part of the patient's body, it is impossible for the patient to treat himself.

Alternatively, a spray gun-type medicine sprayer having the same curing function as that of the poultice has been proposed. This medicine sprayer contains a liquefied medicine. However, if a patient wants to use this spray gun-type medicine sprayer in order to cure an affected part of the patient's body, the patient must press a button for spraying the liquefied medicine so that the medicine is ejected on to the affected part. Therefore, it is inconvenient to use the spray gun-type medicine sprayer. Further, the duration of the curative efficacy of the liquefied medicine in the spray gun-type medicine sprayer is shorter than that of the curative efficacy of the medicine in the poultice.

U.S. Pat. No. 4,676,246, issued to Tetsuya Korenaga on Jun. 30, 1987, discloses a low-frequency electrotherapy apparatus which can be applied to an affected part of a patient's body in a single fitting. Tetsuya Korenaga's low-frequency electrotherapy apparatus includes a main part and a fitting unit electrically connected to the main part through a cable. The fitting unit mainly includes a mounting substrate, a heater, a treating director and a wet pack. The wet pack is wetted by warm or hot water and is secured to the underside of the heater.

In the low-frequency electrotherapy apparatus as described above, the main part of the electrotherapy apparatus is operated such that electric current flows between two electrodes, which are disposed on a diagonal line of the fitting unit, under the state that the electro therapy pack is placed on the affected part of the patient's body. At this time, electric current is supplied from one electrode to the wet pack. Thereby, low-frequency energy is applied to the affected part of the patient's body and stimulates the affected part so that the metabolism of living cells is promoted. As a result, the affected part of the patient's body is cured.

Since the structure of the Tetsuya Korenaga's low-frequency electrotherapy apparatus is complicated, it is difficult to operate this apparatus. Further, since the main part and the fitting unit are connected with each other through the cable, it is inconvenient to use the apparatus.

SUMMARY OF THE INVENTION

The present invention is contrived to solve the foregoing problems. It is an object of the present invention to provide a portable poultice capable of rapidly curing an affected part of a patient's body and of enhancing a curative value by increasing an infiltration efficiency of medicine into a hypodermic tissue of the affected part with the aid of a low-frequency electrotherapy.

In order to achieve the above object, the present invention provides a poultice comprising:

a compress sheet containing a predetermined skin-adhesive medicine adapted to cure an affected part of a patient's body;

a thin film attached to a first surface of the compress sheet in order to protect the skin-adhesive medicine and capable of being detached from the first surface during the use of the poultice;

an attaching sheet for attaching the poultice to the affected part of the patient's body and preventing the compress sheet from being exposed when the poultice is attached to the patient's body;

a low-frequency generating means for generating a low-frequency energy; and conductive layers for transmitting the low-frequency energy to the compress sheet.

The poultice further comprises an operating signal applying means for applying an operating signal to the low-frequency generating means. Preferably, the operating signal applying means comprises a push button. Alternately, a body-temperature sensing sensor or a shock sensing sensor can be used as the operating signal applying means.

A attaching sheet has the total circumference which is greater than that of the compress sheet, and includes skin-adhesive portions having bottom surfaces coated with adhesives. The skin-adhesive portions are provided at opposite ends of the attaching sheet.

The low-frequency generating means includes a main body, an anode terminal and a cathode terminal outwardly protruding from both side surfaces of the main body. The low-frequency generating means is disposed between the conductive layers.

The conductive layers are disposed between the compress sheet and the attaching sheet, and are coated on one surface of the attaching sheet, which is opposite to a second surface of the compress sheet. Meanwhile, terminal grooves for electrically connecting the low-frequency generating means with the conductive layers are formed at one surface of the conductive layers.

As described above, in the poultice according to the present invention, the curative action of the poultice is activated by directly infiltrating a part of the medicine applied on the compress sheets into the hypodermic organism of the affected part and by infiltrating the rest of the medicine into the hypodermic organism of the affected part with the aid of the low-frequency energy. As a result, it is possible to rapidly cure a variety of pains such as a bruise, a muscular pain, an articular disease or neuralgia and to prevent the itching that can be caused by the attachment of the poultice from being generated. Further, it is possible to highly enhance the curative value at a low price.

BRIEF DESCRIPTION OF THE DRAWINGS

The above object and other characteristics and advantages of the present invention will become more apparent by describing in detail a preferred embodiment thereof with reference to the attached drawings, in which.

DETAILED DESCRIPTION OF THE INVENTION

Hereinafter, a preferred embodiment of the present invention will be explained in more detail with reference to the accompanying drawings.

Figure 1:
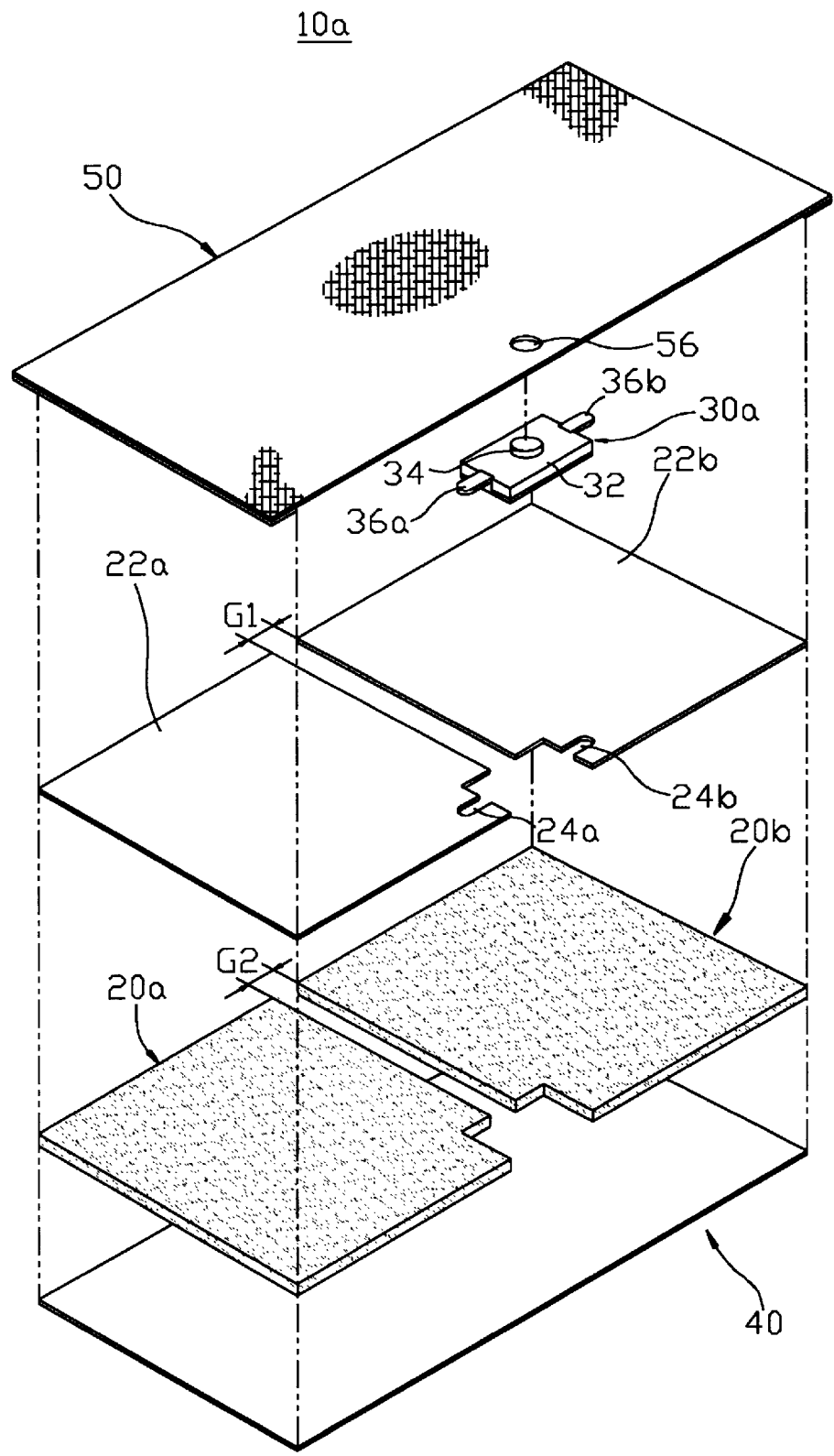
FIG. 1 is an exploded perspective view of a poultice according to a preferred first embodiment of the present invention.

FIG. 1 is an exploded perspective view of a poultice according to a preferred first embodiment of the present invention. Referring to FIG. 1, a poultice 10a according to the preferred first embodiment of the present invention mainly includes a pair of compress sheets 20a, 20b, a pair of conductive layers 22a, 22b, a low-frequency oscillator 30a, a releasable thin film 40 and an attaching sheet 50.

The compress sheets 20a, 20b are composed of flexible woven stuffing which can be separated from each other. Both side surfaces of the compress sheets 20a, 20b are coated with skin-adhesive medicine. A predetermined gap G2 is created between side surfaces of the compress sheets 20a, 20b, which are opposite to each other.

The conductive layers 22a, 22b are disposed between upper surfaces of the compress sheets 20a, 20b and the attaching sheet 50, and are mounted on a bottom surface of the attaching sheet 50, which is opposite to the upper surfaces of the compress sheets 20a, 20b. A predetermined gap G1 is created between side surfaces of the separated conductive layers 22a, 22b, which are opposite to each other. The size of the gap G2 is the same as that of the gap G1. Terminal grooves 24a, 24b for electrically connecting the low-frequency oscillator 30a with the conductive layers 22a, 22b are formed at side surfaces of the conductive layers 22a, 22b, respectively, which are opposite to each other.

The low-frequency oscillator 30a includes a circuit controlling an alarm displaying function or a lamp displaying function. The low-frequency oscillator 30a includes a main body 32 of which a battery is included therein, and an anode terminal 36a and a cathode terminal 36b outwardly protruding from opposite side surfaces of the main body 32. A push button 34 protrudes from an upper surface of the main body 32 of the low-frequency oscillator 30a. The push button 34 applies an operating signal to the low-frequency oscillator 30a when a patient presses the push button 34 with his hand. The low-frequency oscillator 30a is disposed between the conductive layers 22a, 22b by inserting the anode terminal 36a and the cathode terminal 36b into the terminal grooves 24a, 24b which are formed at opposing side surfaces of the conductive layers 22a, 22b respectively.

Meanwhile, a battery capacity of the low-frequency oscillator 30a can be set at a predetermined value such that the battery of the low-frequency oscillator 30a can generate an electric current for an anticipated period of efficacy the of medicine in the compress sheets 20a, 20b. Accordingly, if the battery of the low-frequency oscillator 30a dies, the patient can precisely identity the need to replace the poultice 10a due to the alarm displaying function and/or the lamp displaying function of the low-frequency oscillator 30a.

Alternatively, the battery capacity of the low-frequency oscillator 30a can be set at a predetermined value such that the battery of the low-frequency oscillator 30a can generate an electric current for a duration of time until the used compress sheets 20a, 20b are to be replaced by new compress sheets 20a, 20b in accordance with predetermined replacing times during the patient's use of poultice 10a. Therefore, it is possible to use the poultice 10a so that the compress sheets 20a, 20b are only replaced as occasion demands.

The releasable thin film 40 for protecting the medicine applied on the bottom surfaces of the compress sheets 20a, 20b can be made of flexible vinyl. The releasable thin film 40 can be detached from the poultice 10a at the time that the patient attaches the poultice 10a to the affected part of the patient's body.

The conductive layers 22a, 22b are deposited onto the lower surfaces of the attaching sheet 50. That is, the conductive layers 22a, 22b are coated onto the lower surfaces of the attaching sheet 50 after the anode terminal 36a and the cathode terminal 36b of the low-frequency oscillator 30a have been inserted into the terminal grooves 24a, 24b of the conductive layers 22a, 22b, respectively. A button hole 56 is formed through the attaching sheet 50 so that it is aligned with the push button 34 of the low-frequency oscillator 30a which is disposed between the conductive layers 22a,22b. Therefore, if the attaching sheet 50 is attached to the upper surfaces of the compress sheets 20a,20b, the push button 34 of the low-frequency oscillator 30a is exposed external to the poultice 10a through the button hole 56.

Figure 2:
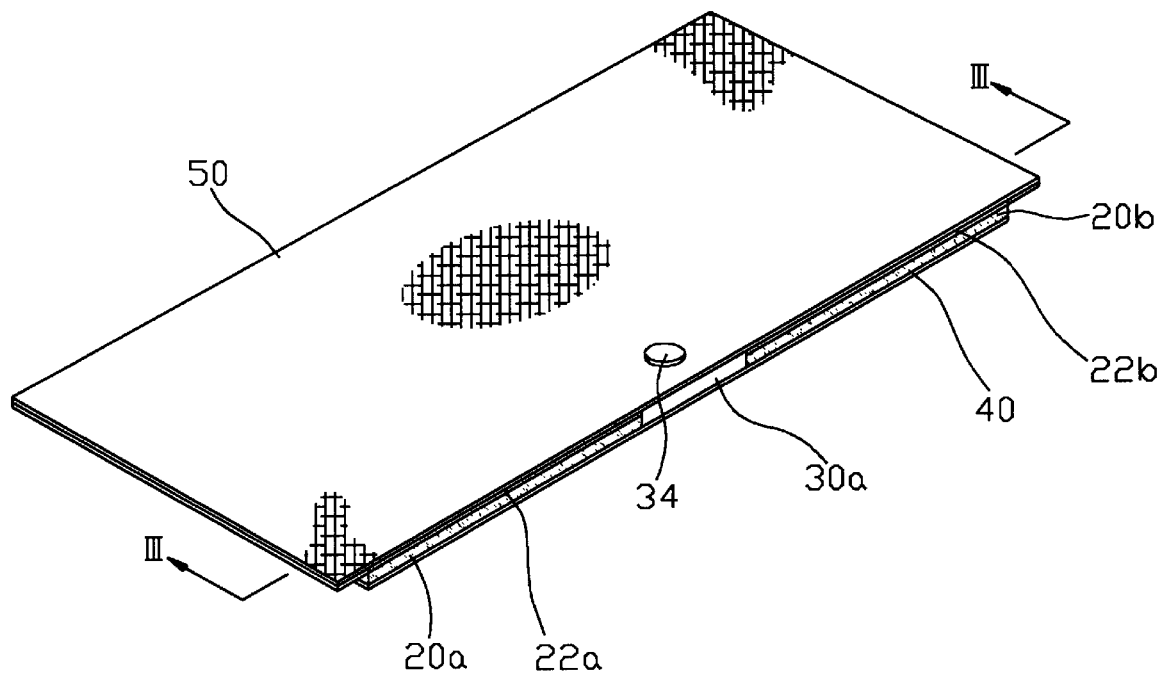
FIG. 2 is a perspective view of the poultice according to the preferred first embodiment of the present invention.
Figure 3:
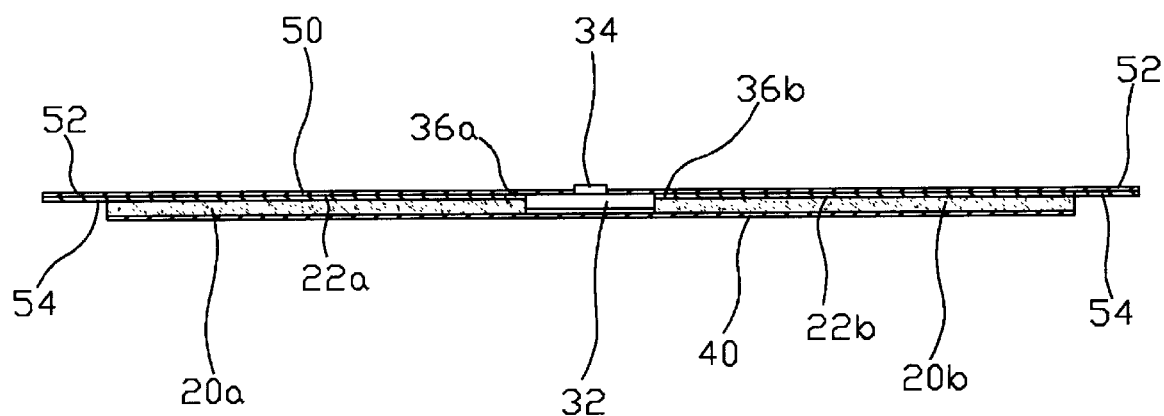
FIG. 3 is a sectional view taken along the line III—III of FIG. 2.
Figure 4:
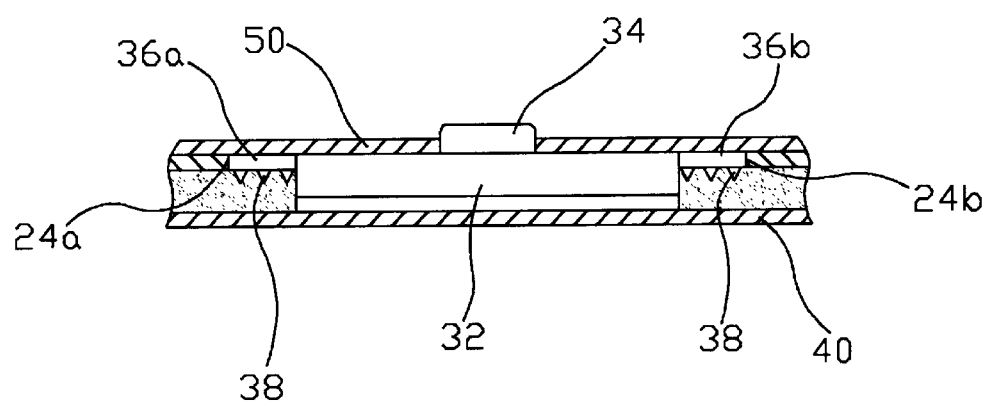
FIG. 4 is an enlarged view of an important part of the poultice illustrated in FIG. 3.

FIG. 2 is a perspective view of the poultice according to the preferred first embodiment of the present invention, FIG. 3 is a sectional view taken along the line III—III of FIG. 2, and FIG. 4 is an enlarged view of an important part of the poultice illustrated in FIG. 3.

Referring to FIGS. 2 to 4, the poultice 10a is integrally formed by laminating the pair of compress sheets 20a, 20b, the releasable thin film 40 and the attaching sheet 50 to form a plate-shaped structure. The attaching sheet 50 has a total circumference viewed in a direction perpendicular to the adjacent surfaces of the attaching sheet 50 and the compress sheets 20a, 20b greater than that of the compress sheets 20a, 20b so that the upper surfaces of the compress sheets 20a, 20b are not exposed external to the poultice 10a. Further, skin-adhesive portions 52 are provided at both distal ends of the attaching sheet 50. Bottom surfaces of the skin-adhesive portions 52 are coated with predetermined adhesives. The bottom surfaces of the skin-adhesive portions 52 are protected by the skin-adhesive tapes 54. The skin-adhesive portions 52 can be directly attached to the affected part of the patient's body without trouble (such as adhesion obstruction by the compress sheets 20a, 20b) by detecting the skin-adhesive tapes 54 from the skin-adhesive portions 52 and attaching the poultice 10a to the affected part. Thereby, the poultice 10a is firmly attached to the affected part of the patient's body.

Meanwhile, the low-frequency oscillator 30a is disposed between the conductive layers 22a, 22b by inserting the anode terminal 36a and the cathode terminal 36b into the terminal grooves 24a, 24b which are formed at opposing side surfaces of the conductive layers 22a, 22b respectively. A plurality of locking protrusions 38 downwardly protrude from lower surfaces of the anode terminal 36a and the cathode terminal 36b. The locking protrusions 38 firmly fix the anode terminal 36a and the cathode terminal 36b to the upper surfaces of the compress sheets 20a, 20b when the attaching sheet 50, of which the conductive layers 22a, 22b are coated on the lower surfaces thereof, and the compress sheets 20a, 20b are combined with each other.

Figure 5A:
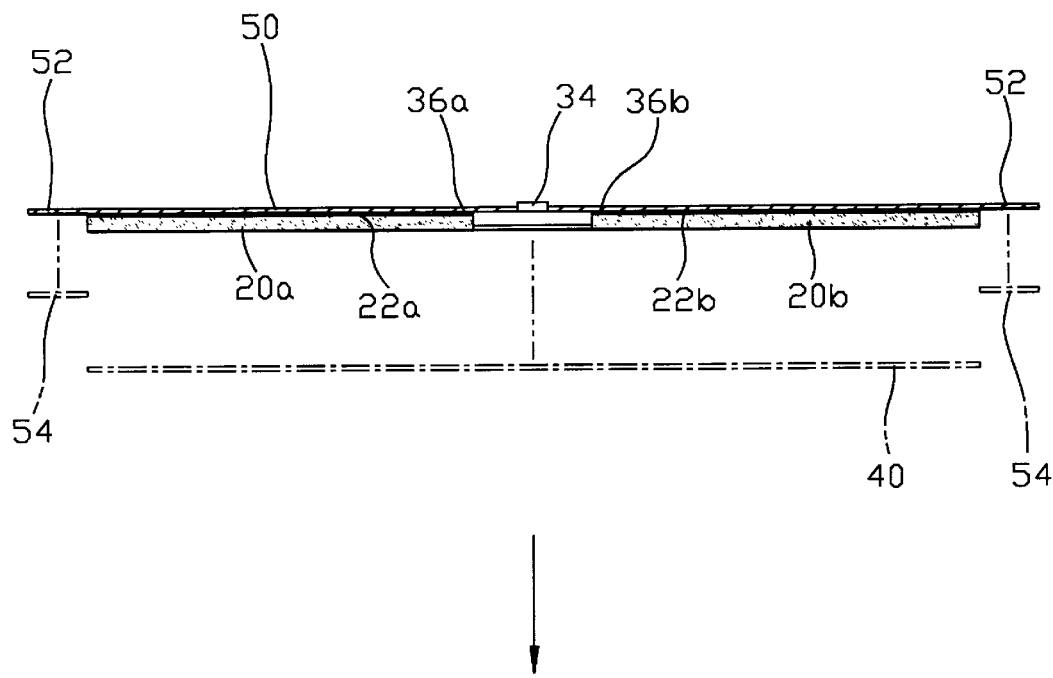
FIGS. 5A and 5B show use of the poultice according to the preferred first embodiment of the present invention.
Figure 5B:
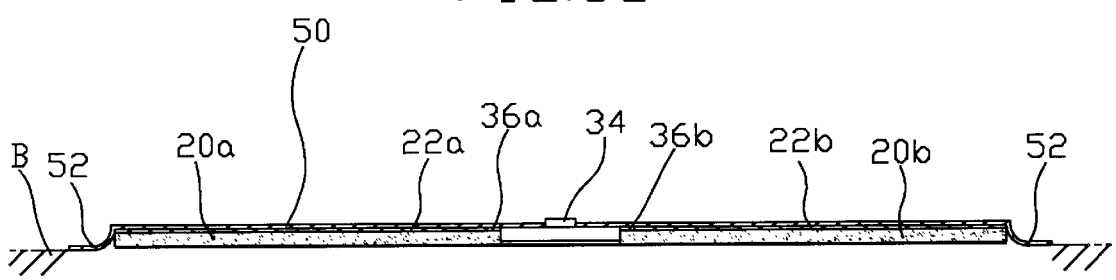

FIGS. 5A and 5B show use of the poultice according to the preferred first embodiment of the present invention. Herein below, a method of using the poultice 10a as described above will be described with reference to FIGS. 5A and 5B.

When a patient having a wound such as a bruise, a muscular pain, an articular disease, neuralgia or the like wants to use the poultice 10a according to the preferred first embodiment of the present invention, the patient detaches the releasable thin film 40 from the bottom surfaces of the compress sheets 20a, 20b and detaches the skin-adhesive tape 54 covering the skin-adhesive portions 52 of the attaching sheet 50 from the skin-adhesive portions 52.

Thereafter, the patient contacts the bottom surfaces of the compress sheets 20a, 20b on which the skin-adhesive medicine is applied with the affected part (B), and presses the upper surface of the attaching sheet 50 and the skin-adhesive portion 52 by the hands. Thereby, the compress sheets 20a, 20b are attached to the affected part (B). At this time, the compress sheets 20a, 20b are firmly attached to the affected part (B) by means of the skin-adhesive medicine and the skin-adhesive portion 52.

In this state, as shown in FIG. 5B, if the patient presses the push button 34, which is external to the poultice 10a through the button hole 56 of the attaching sheet 50, with his hand, an operating signal generated by the push button 34 is applied to the low-frequency oscillator 30a, and thereby the low-frequency oscillator 30a begins to operate. Then, a low-frequency energy generated from the low-frequency oscillator 30a is transmitted to the conductive layers 22a, 22b which are coated on the bottom surface of the attaching sheet 50.

The low-frequency energy transmitted from the low-frequency oscillator 30a to the conductive layers 22a, 22b infiltrates into hypodermic organisms of the affected part (B) through the compress sheets 20a, 20b and stimulates the affected part (B) so that the metabolism of living cells is promoted. Further, the low-frequency energy rapidly and uniformly transfers composition of the medicine from the bottom surfaces of the compress sheets 20a,20b into the hypodermic organisms of the affected part (B).

The medical action due to the low-frequency is activated by joining a low frequency vibration of an anode with a low-frequency vibration of a cathode, which are generated from the anode terminal 36a and the cathode terminal 36b and pass through the compress sheet 20a, 20b, respectively.

However, when the battery capacity of the low-frequency oscillator 30a is set at a predetermined value such that the battery in the low-frequency oscillator 30a can generate an electric current for an anticipated period of efficacy of the medicine in the compress sheets 20a,20b, if the battery of the low-frequency oscillator 30a in the poultice 10a attached to the affected part (B) dies, the patient identifies the fact that the efficacy of medicine in the compress sheets 20a, 20b has ended due to the alarm displaying function and/or the lamp displaying function of the low-frequency oscillator 30a. At this time, if the patient wants to continuously cure the affected part (B), it is necessary to remove the worn poultice 10a and to attach a new poultice 10a to the affected part (B). Then, it is possible to obtain a continuously curative effect.

Alternatively, when the battery capacity of the low-frequency oscillator 30a is set a predetermined value such that the battery of the low-frequency oscillator 30a can generate an electric current for a duration of time until the used compress sheets 20a,20b are to be replaced by new compress sheets 20a, 20b in accordance with predetermined replacing times during the patient's use of poultice 10a the poultice 10a, if the efficacy of medicine in the compress sheets 20a, 20b has ended, the patient identifies this fact due to the alarm displaying function and/or the lamp displaying function of the low-frequency oscillator 30a. At this time, if the patient wants to continuously cure the affected part (B), it is necessary to remove the used compress sheets 20a,20b from the poultice 10a and to attach new compress sheets 20a,20b to the bottom surface of the attaching sheet 50. Then, it is possible to obtain a continuously curative effect.

Figure 6:
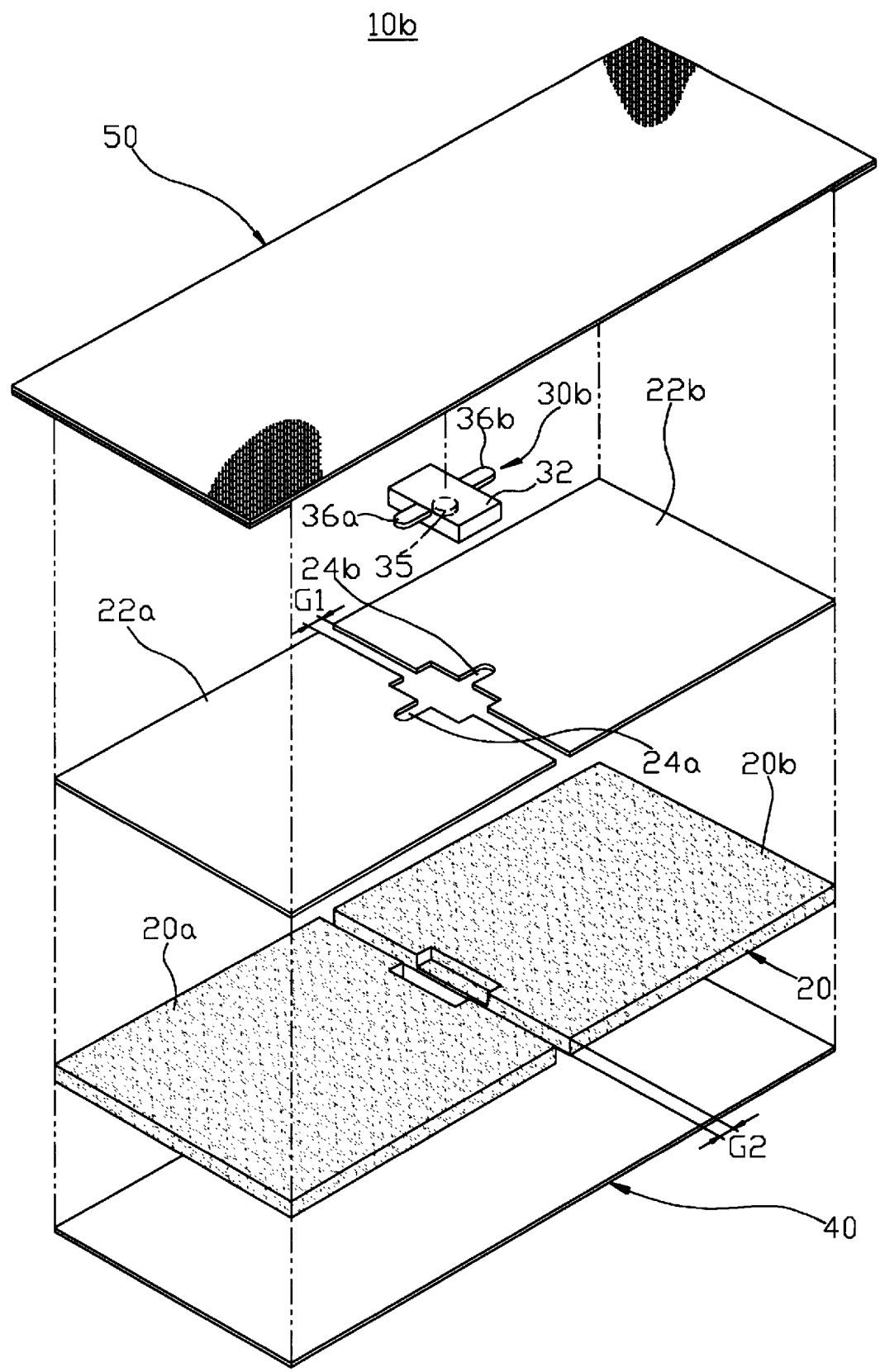
FIG. 6 is an exploded perspective view of a poultice according to a preferred second embodiment of the present invention.
Figure 7:
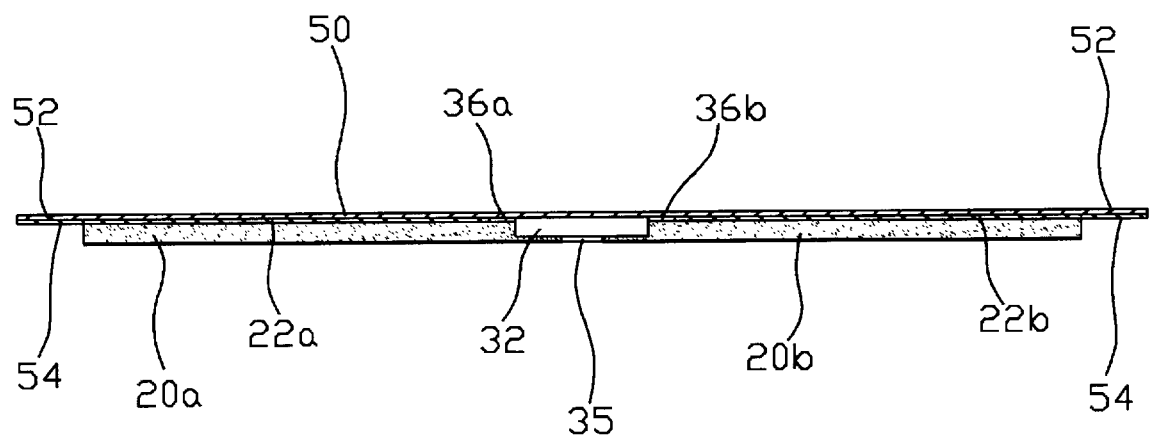
FIG. 7 is a longitudinal sectional view of the poultice according to the preferred second embodiment of the present invention.

FIG. 6 is an exploded perspective view of a poultice according to a preferred second embodiment of the present invention, and FIG. 7 is a longitudinal sectional view of the poultice according to the preferred second embodiment of the present invention.

The poultice 10b according to the preferred second embodiment of the present invention has the same constitution as that of the poultice 10a according to the preferred first embodiment of the present invention except for a body-temperature sensing sensor or a shock sensing sensor 35 installed in the low-frequency oscillator 30a. Accordingly, descriptions of constitutional elements which are identical to the constitutional elements of the poultice 10a according to the preferred first embodiment of the present invention will be omitted. Further, inventive elements which are identical to the inventive elements used in the preferred first embodiment of the present invention have the same reference numerals.

Referring to FIGS. 6 and 7, in the poultice 10b according to the preferred second embodiment of the present invention, the low-frequency oscillator 30b includes a circuit controlling an alarm displaying function or a lamp displaying function. The low-frequency oscillator 30b includes a main body 32 of which a battery is included therein, and an anode terminal 36a and a cathode terminal 36b outwardly protruding from opposite side surfaces of the main body 32. The body-temperature sensing sensor or the shock sensing sensor 35 is installed on the lower surface of the main body 32. When the patient attaches the poultice 10b on the affected part (B) of the patient's body, the body-temperature sensing sensor or the shock sensing sensor 35 applies an operating signal to the low-frequency oscillator 30b in response to sensing the temperature of the patient's body or the shock being applied to the poultice 10b during the attachment of the poultice 10b. The low-frequency oscillator 30b is disposed between the conductive layers 22a,22b by inserting the anode terminal 36a and the cathode terminal 36b into the terminal grooves 24a, 24b which are formed at opposing side surfaces of the conductive layers 22a, 22b, respectively.

Meanwhile, a battery capacity of the low-frequency oscillator 30b can be set at a predetermined value such that the battery of the low-frequency oscillator 30b can generate an electric current for an anticipated period of efficacy of the medicine in the compress sheets 20a, 20b. Alternatively, the battery capacity of the low-frequency oscillator 30b can be at a predetermined value such that the battery of the low-frequency oscillator 30b can generate an electric current for a duration of time until the used compress sheets 20a,20b are to be replaced by new compress sheets 20a, 20b in accordance with predetermined replacing times during the patient's use of the poultice 10a. Therefore, the patient can use the poultice 10b by replacing the used poultice 10b with a new poultice 10b or only by replacing the used compress sheets 20a,20b with new compress sheets 20a,20b as occasion demands after the patient identifies the need to replace the poultice 10b or the compress sheets 20a, 20b due to the alarm displaying function and/or the lamp displaying function of the low-frequency oscillator 30a.

Hereinbelow, a method of using the poultice 10b as described above will be described.

When a patient having a wound such as a bruise, a muscular pain, an articular disease, neuralgia or the like wants to use the poultice 10b according to the preferred second embodiment of the present invention, the patient detaches the releasable thin film 40 from the bottom surfaces of the compress sheets 20a, 20b and detaches the skin-adhesive tape 54 covering the skin-adhesive portions 52 of the attaching sheet 50 from the skin-adhesive portions 52.

Thereafter, the patient contacts the bottom surfaces of the compress sheets 20a,20b on which the skin-adhesive medicines are applied with the affected part (B), and presses the upper surface of the attaching sheet 50 and the skin-adhesive portion 52 by the hands. Thereby, the compress sheets 20a,20b are attached to the affected part (B). At this time, the compress sheets 20a,20b are firmly attached to the affected part (B) by means of the skin-adhesive medicine and the skin-adhesive portion 52.

In this state, the body-temperature sensing sensor or the shock sensing sensor 35 installed on the lower surface of the main body 32 applies an operating signal to the low-frequency oscillator 30b in response to sensing the temperature of the patient's body or the shock being applied to the poultice 10b during the attachment of the poultice 10b. As a result, the low-frequency oscillator 30b begins to operate, and thereby a low-frequency energy being generated from the low-frequency oscillator 30b is transmitted to the conductive layers 22a,22b, which are coated on the bottom surface of the attaching sheet 50, through the anode terminal 36a and the cathode terminal 36b.

The low-frequency energy transmitted from the low-frequency oscillator 30b to the conductive layers 22a, 22b infiltrates into hypodermic organisms of the affected part (B) through the compress sheets 20a, 20b and stimulates the affected part (B) so that the metabolism of living cells is promoted. Further, the low-frequency energy rapidly and uniformly transfers compositions of the medicines to be diffused into the hypodermic organisms of the affected part (B) from the bottom surfaces of the compress sheets 20a, 20b.

The medical action due to the low-frequency is activated by joining a low frequency vibration of an anode with a low-frequency vibration of a cathode, which are generated from the anode terminal 36a and the cathode terminal 36b and pass through the compress sheet 20a, 20b, respectively.

As described above, in the poultices 10a, 10b according to the preferred first and second embodiments of the present invention, the medical action of the poultices 10a, 10b is activated by directly infiltrating a part of the medicine applied on the compress sheets 20a,20b into the hypodermic organism of the affected part (B) and by infiltrating the rest of the medicine into the hypodermic organism of the affected part (B) with the aid of the low-frequency energy. As a result, it is possible to rapidly cure a variety of pains such as a bruise, a muscular pain, an articular disease or neuralgia and to prevent the itching that can be caused by the attachment of the poultice from being generated. Further, it is convenient to use the poultices 10a, 10b. In addition, it is possible to highly enhance the curative value at a low price.

While the present invention has been particularly shown and described with reference to particular embodiments thereof, it will be understood by those skilled in the art that various changes in form and details may be effected therein without departing from the spirit and scope of the invention as defined by the appended claims.

What is claimed is:

1. A poultice, comprising:
    a compress sheet containing a predetermined skin-adhesive medicine for an affected part of a patient's body;
    a film attached to a first surface of said compress sheet in order to protect the skin-adhesive medicine and capable of being detached from the first surface during the use of the poultice;
    an attaching sheet for attaching the poultice to the affected part of the patient's body and preventing said compress sheet from being exposed when the poultice is attached to the patient's body;
    a low-frequency generating means for generating a low-frequency energy;
    conductive layers for transmitting the low-frequency energy to said compress sheet;
    an operating signal applying means for applying an operating signal to said low-frequency generating means; and wherein said operating signal applying means comprises a push button which is installed at one surface of said low-frequency generating means and protrudes from the one surface.

2. A poultice as in claim 1, wherein said push button is exposed external to the poultice through a hole formed through a center portion of said attaching sheet when said attaching sheet is positioned on a second surface of said compress sheet opposite said first surface, and said push button is adapted to apply the operating signal to said low-frequency generating means when the patient presses said push button.

3. A poultice, comprising:
- a compress sheet containing a predetermined skin-adhesive medicine for an affected part of a patient's body;
- a film attached to a first surface of said compress sheet in order to protect the skin-adhesive medicine and capable of being detached from the first surface during the use of the poultice;
- an attaching sheet for attaching the poultice to the affected part of the patient's body and preventing said compress sheet from being exposed when the poultice is attached to the patient's body;
- a low-frequency generating means for generating a low-frequency energy;
- conductive layers for transmitting the low-frequency energy to said compress sheet;
- an operating signal applying means for applying an operating signal to said low-frequency generating means; and
- wherein said operating signal applying means comprises a body-temperature sensing sensor installed on one surface of said low-frequency generating means.

4. A poultice as in claim 3, wherein said body-temperature sensing sensor is adapted to apply the operating signal to said low-frequency generating means in response to sensing the body temperature of the patient when the patient attaches the poultice to the affected part of the patient's body.

5. A poultice, comprising:
- a compress sheet containing a predetermined skin-adhesive medicine for an affected part of a patient's body;
- a film attached to a first surface of said compress sheet in order to protect the skin-adhesive medicine and capable of being detached from the first surface during the use of the poultice;
- an attaching sheet for attaching the poultice to the affected part of the patient's body and preventing said compress sheet from being exposed when the poultice is attached to the patient's body;
- a low-frequency generating means for generating a low-frequency energy;
- conductive layers for transmitting the low-frequency energy to said compress sheet;
- an operating signal applying means for applying an operating signal to said low-frequency generating means; and
- wherein said operating signal applying means comprises a shock sensing sensor installed on one surface of said low-frequency generating means.

6. A poultice as in claim 5, wherein said shock sensing sensor is adapted to apply the operating signal to said low-frequency generating means in response to sensing shock applied to the poultice at the time that the patient attaches the poultice to the affected part of the patient's body.

7. A poultice as in claim 1, wherein said attaching sheet has a total circumference, viewed in a direction perpendicular to adjacent surfaces of the attaching sheet and compress sheet, greater than that of said compress sheet, and includes skin-adhesive portions having bottom surfaces coated with adhesives, said skin-adhesive portions being provided at opposite ends of said attaching sheet, and wherein a hole is formed through a center portion of said attaching sheet.

8. A poultice as in claim 1, 5, or 7, wherein said low-frequency generating means includes a main body, an anode terminal and a cathode terminal outwardly protruding from opposite side surfaces of said main body, said low-frequency generating means is disposed between said conductive layers by inserting said anode terminal and said cathode terminal into terminal grooves for electrically connecting said low-frequency generating means with said conductive layers, said terminal grooves being formed at opposing side surfaces of said conductive layers.

9. A poultice as in claim 1, 5, or 7, wherein said conductive layers are disposed between said compress sheet and said attaching sheet, said conductive layers are coated on one surface of said attaching sheet, which is opposite to a second surface of said compress sheet opposite said first surface, and wherein terminal grooves for electrically connecting said low-frequency generating means with said conductive layers are formed at opposing side surfaces of said conductive layers.

10. A poultice, comprising:
- a compress sheet containing a predetermined skin-adhesive medicine for an affected part of a patient's body;
- a film attached to a first surface of said compress sheet in order to protect the skin-adhesive medicine and capable of being detached from the first surface during the use of the poultice;
- an attaching sheet for attaching the poultice to the affected part of the patient's body and preventing said compress sheet from being exposed when the poultice is attached to the patient's body, said attaching sheet having a total circumference, viewed in a direction perpendicular to adjacent surfaces of the attaching sheet and compress sheet, greater than that of said compress sheet, said attaching sheet including skin-adhesive portions having bottom surfaces coated with adhesives, said skin-adhesives portion being provided at opposite ends of said attaching sheet, and wherein a hole is formed through a center portion of said attaching sheet;
- a low-frequency generating means for generating a low-frequency energy, said low-frequency generating means including a main body, an anode terminal and a cathode terminal outwardly protruding from opposite side surfaces of said main body;
- conductive layers for transmitting the low-frequency energy to said compress sheet, said conductive layers being disposed between said compress sheet and said attaching sheet, said conductive layers being coated on one surface of said attaching sheet, which is opposite to a second surface of said compress sheet opposite said first surface, and wherein terminal grooves for electrically connecting said low-frequency generating means with said conductive layers are formed at opposing side surfaces of said conductive layers; and
- an operating signal applying means for applying an operating signal to said low-frequency generating means.

11. A poultice as in claim 10, wherein said operating signal applying means comprises a push button which is installed at one surface of said low-frequency generating means and protrudes from the surface.

12. A poultice as in claim 11, wherein said push button is exposed external to the poultice through a hole formed through a center portion of said attaching sheet when said attaching sheet is positioned on the second surface of said compress sheet, and said push button is adapted to apply the operating signal to said low-frequency generating means when the patient presses said push button.

13. A poultice as in claim 10, wherein said operating signal applying means comprises a body-temperature sensing sensor installed on one surface of said low-frequency generating means.

14. A poultice as in claim 13, wherein said body-temperature sensing sensor is adapted to apply the operating signal to said low-frequency generating means in response to sensing the body temperature of the patient when the patient attaches the poultice to the affected part of the patient's body.

15. A poultice as in claim 10, wherein said operating signal applying means comprises a shock sensing sensor installed on one surface of said low-frequency generating means.

16. A poultice as in claim 15, wherein said shock sensing sensor is adapted to apply the operating signal to said low-frequency generating means in response to sensing shock applied to the poultice at the time that the patient attaches the poultice to the affected part of the patient's body.

17. A poultice as in claim 10, wherein said low-frequency generating means is disposed between said conductive layers by inserting said anode terminal and said cathode terminal into said terminal grooves.

18. A poultices comprising:

a compress sheet containing a predetermined skin-adhesive medicine for an affected part of a patient's body;

a thin film attached to a first surface of said compress sheet in order to protect the skin-adhesive medicine and capable of being detached from the first surface during the use of the poultice;

an attaching sheet for attaching the poultice to the affected part of the patient's body and preventing said compress sheet from being exposed when the poultice is attached to the patient's body, said attaching sheet having a total circumference, viewed in a direction perpendicular to adjacent surfaces of the attaching sheet and compress sheet, greater than that of said compress sheet, said attaching sheet including skin-adhesive portions having bottom surfaces coated with adhesives, said skin-adhesive portions provided at opposite ends of said attaching sheet, and wherein a hole is formed through a center portion of said attaching sheet;

a low-frequency generating means for generating a low-frequency energy, said low-frequency generating means including a main body, an anode terminal and a cathode terminal outwardly protruding from opposite side surfaces of said main body;

conductive layers for transmitting the low-frequency energy to said compress sheet, said conductive layers being disposed between said compress sheet and said attaching sheet, said conductive layers being coated on one surface of said attaching sheet, which is opposite to a second surface of said compress sheet opposite said first surface, and wherein terminal grooves for electrically connecting said low-frequency generating means with said conductive layers are formed at opposing side surfaces of said conductive layers; and a push button for applying an operating signal to said low-frequency generating means, said push button being installed at one surface of said low-frequency generating means and protruding from the surface, said push button being exposed external to the poultice through said hole when said attaching sheet is positioned on the second surface of said compress sheet, and said push button is adapted to apply the operating signal to said low-frequency generating means when the patient presses said push button.

* * * * *